United States Patent [19]

Shereda et al.

[11] 4,157,033
[45] Jun. 5, 1979

[54] SPRING TESTER

[75] Inventors: Daniel J. Shereda, Redford; Tilak R. Sahni, Plymouth, both of Mich.

[73] Assignee: Link Engineering Company, Detroit, Mich.

[21] Appl. No.: 832,736

[22] Filed: Sep. 12, 1977

[51] Int. Cl.² ............................................. G01L 1/04
[52] U.S. Cl. ..................................................... 73/161
[58] Field of Search ............................ 73/161, 94, 100

[56] References Cited
U.S. PATENT DOCUMENTS

| | | | |
|---|---|---|---|
| 3,165,926 | 1/1965 | Orr et al. | 73/161 |
| 3,206,971 | 9/1965 | Felix | 73/141 A |
| 3,285,065 | 11/1966 | Ragen et al. | 73/161 |

Primary Examiner—Richard C. Queisser
Assistant Examiner—Joseph W. Roskos

[57] ABSTRACT

Disclosed is an improved device for testing the compression, tension, or spring rate of a spring or other resilient material. The device is adapted to automatically display the load reading of a spring at a preselected height by merely compressing the spring past the check point. Alternatively, additional displays may be provided so that load readings at different height settings can be displayed with a single compression of the spring through all of the check points. In addition, the rate of a spring can be readily determined by setting two check points a unit distance apart and utilizing the load reading from the first check point to establish the reference level of the meter. The spring tester includes an electronic control circuit comprising a plurality of sample and hold circuits and a corresponding plurality of thumbwheel comparators. The comparators are connected to a height indicator and each is adapted to provide an output signal when the height of the spring corresponds to the preset height of the comparator. Each sample and hold circuit is connected to the load cell and to one of the comparators and is adapted to provide an output signal that follows the force reading from the load cell until the output signal from its respective comparator is received. When this occurs, the sample and hold circuit "holds" the current force reading of the load cell despite further compression of the spring.

11 Claims, 5 Drawing Figures

SPRING TESTER

BACKGROUND & SUMMARY OF THE INVENTION

The present invention relates to a spring tester, and in particular to a spring testing device that is capable of providing a load reading at a particular height merely by compressing the test object past the desired check point.

With conventional spring testing devices, in order to obtain a force reading at a desired height, the operator must compress the spring to the desired check point and attempt to maintain the spring at that height for a sufficient period of time to ascertain the correct load reading. As can be readily appreciated, the greater the compression force of the spring, the more difficult it becomes to maintain the spring at the desired compressed height in order to obtain a proper load reading. Furthermore, if a load reading is desired at several different heights, the same procedure must be repeated for each reading. In addition, if the spring rate of a spring is desired, it is necessary to take a reading at a first height, another reading at a second height, and then subtract the two readings. Thus, the inconvenience, the amount of time required, and the potential inaccuracies in obtaining load readings utilizing a conventional spring tester are apparent.

Mechanically operated compressor type spring testing devices are available that employ accurate mechanical stops to eliminate the need for having to manually hold the spring at the desired height setting. However, such devices are substantially more expensive than the manually operated units, and still do not have the capability of obtaining spring rate readings or multiple force readings with a single compression of the test spring.

The present invention provides an improved spring testing device that permits a user to obtain a particular load reading at a preselected height without having to maintain the spring at the desired compressed height. In addition, the present spring tester can provide spring rate readings and multiple force readings with a single compression of the test spring. The spring tester according to the present invention is adapted to provide a load reading at a preselected height merely by compressing the spring past the appropriate check point. The force reading from that setting is automatically retained and displayed on a digital voltmeter or other display device. Thus, the disadvantage of having to manually maintain the spring at the appropriate compressed height is avoided. The present spring tester can also, as noted, provide a spring rate reading with a single compression of the test spring. In particular, by selecting two check points a unit distance apart, and setting the digital display to "rate", the first load reading is utilized to establish the zero reference for the meter so that the reading displayed when the second check point is reached corresponds to the spring rate of the spring.

The present invention includes an electronic control circuit which, in general, comprises a sample and hold circuit that is connected to receive the output from the force transducer mounted in the base of the compressor unit. The output signal from the sample and hold circuit, which is provided to a digital voltmeter, is adapted to follow the signal provided to its input from the load cell. A height indicator, which produces a signal representative of the height of the spring, is connected to a thumbwheel comparator that is adapted to be preset to the height at which the desired load reading is to be taken. When the output signal from the height indicator equals the preselected height, the comparator provides an output signal that is supplied to the sample and hold circuit and is effective to cause the sample and hold circuit to maintain at its output the current load cell reading. Thus, it is apparent that the spring may be compressed past the desired check point and the load reading at the preselected height will be automatically retained.

The control circuit is capable of producing spring rate readings by providing an additional thumbwheel comparator that is connected to a second sample and hold circuit. The output from the second sample and hold circuit is provided to the reference input of the digital voltmeter. Thus, the spring rate of a spring is determined merely by presetting the two comparators to heights a unit distance apart, and compressing the spring through both check points. The output from the second sample and hold circuit provides the zero reference for the voltmeter so that the load reading displayed on the meter when the second check point is passed will correspond to the difference in the load readings at the preselected heights.

Additionally, it will be seen that the present invention can be readily adaptable to provide any number of lead readings at different heights with a single compression of the spring, by adding duplicate circuitry and additional meters. Further objects and advantages of the present invention will become apparent from a reading of the detailed description of the preferred embodiments which makes reference to the following set of drawings in which:

BRIEF DESCRIPTION OF THE DRAWINGS

FIG. 4 is a circuit diagram of the remainder of the electronic control circuit of FIG. 2; and FIG. 5 is a simplified circuit diagram of a sample and hold circuit.

DETAILED DESCRIPTION OF THE PREFERRED EMBODIMENTS

Figure 1:
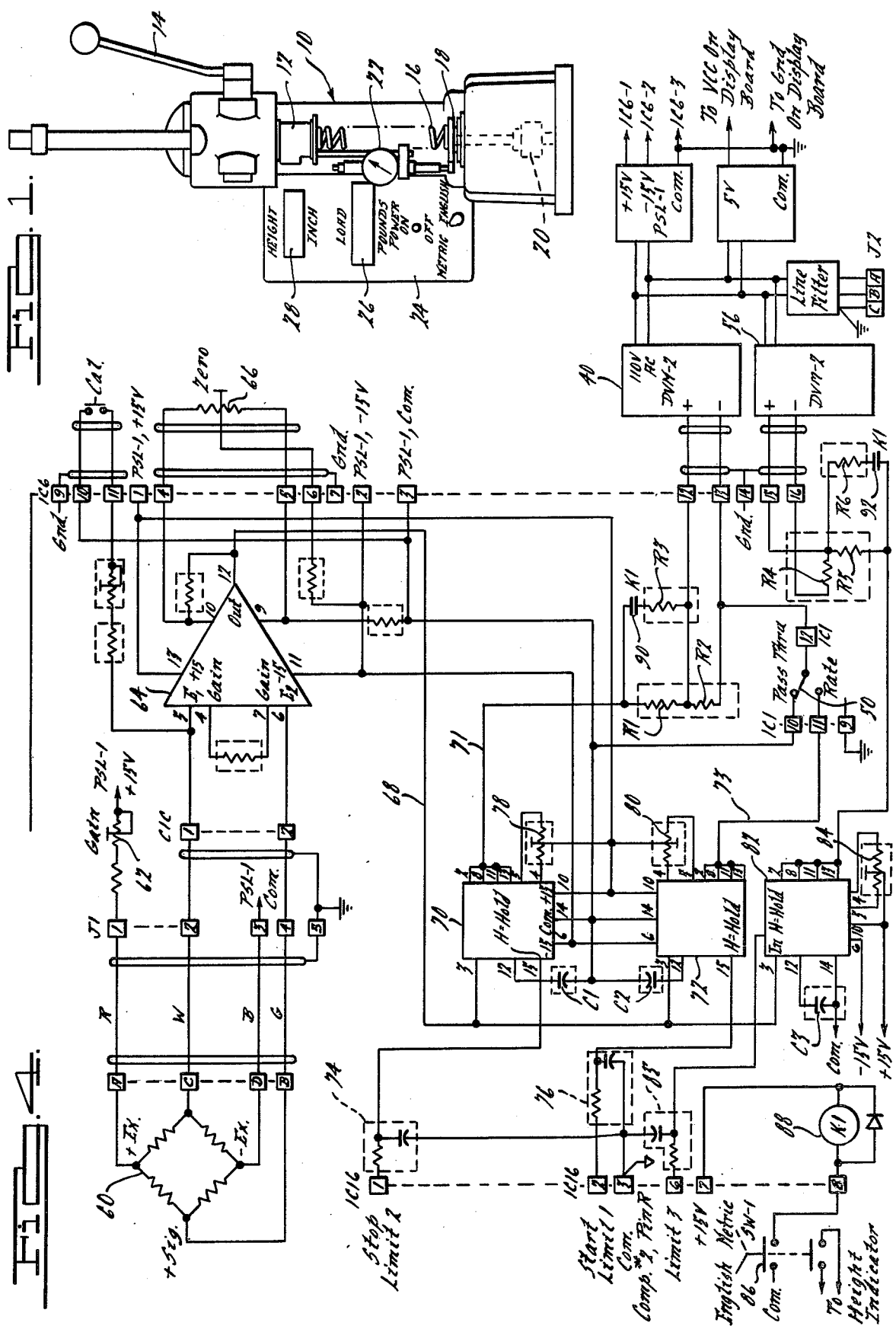
FIG. 1 is a plan view of a spring tester unit.

Referring to FIG. 1, an improved spring tester according to the present invention is shown. In general, the compressor unit 10 comprises a ram 12 that is raised or lowered by a manually operated rotating arm 14. When lowered, the ram 12 is adapted to compress the test spring 16, or other resilient material, against the plate 18 fastened to the base of the unit 10. Mounted to the plate 18 is a force transducer 20, such as a strain gauge load cell, that is adapted to produce an electrical signal having a voltage level that is directly related to the amount of force exerted on the load cell 20 by the spring 16. A height indicator 22 is fastened to the unit between ram 12 and plate 18 and is adapted to provide an output signal that is directly related to the height of the spring 16.

A tension bridge attachment (not shown) may be fastened to the ram 12 for testing the load characteristics of tension springs as well. Importantly, it is to be understood that, although the operation of the present invention will be described in relation to the testing of compression springs, it is not to be inferred that the present invention is limited to compression testing only. Rather, as will be readily apparent to those skilled in the art, the principles of the present invention are equally adaptable to the testing of tension springs. Further, it is to be understood that the term "compression" as it is used in the adjoining claims to describe the claimed testing apparatus, is intended to include the opposite procedure of testing tension as well.

The electronic control circuit of the present invention is housed within the display unit 24 which may be located adjacent to or remote from the compressor unit 10. The preferred embodiment includes a digital voltmeter 26 for displaying the load reading. However, any suitable type of voltmeter may be used. The control unit may even be interfaced with a printer for providing a hard copy of the load readings taken. In addition, a switch 25 located on the front panel of the display unit 24 is provided so that the readings can be displayed in either English or Metric units. Optionally, a digital display 28 for providing a read-out of the height indicator 22 may also be included.

Although FIG. 1 depicts a manually operated compressor, it is to be understood that the present invention can also be utilized in combination with a mechanically operated spring tester. As will be appreciated by those skilled in the art, the adaptation of the present system to a mechanically operated unit eliminates the need for accurate mechanical stops, and thus substantially reduces the cost of such a unit.

Figure 2:
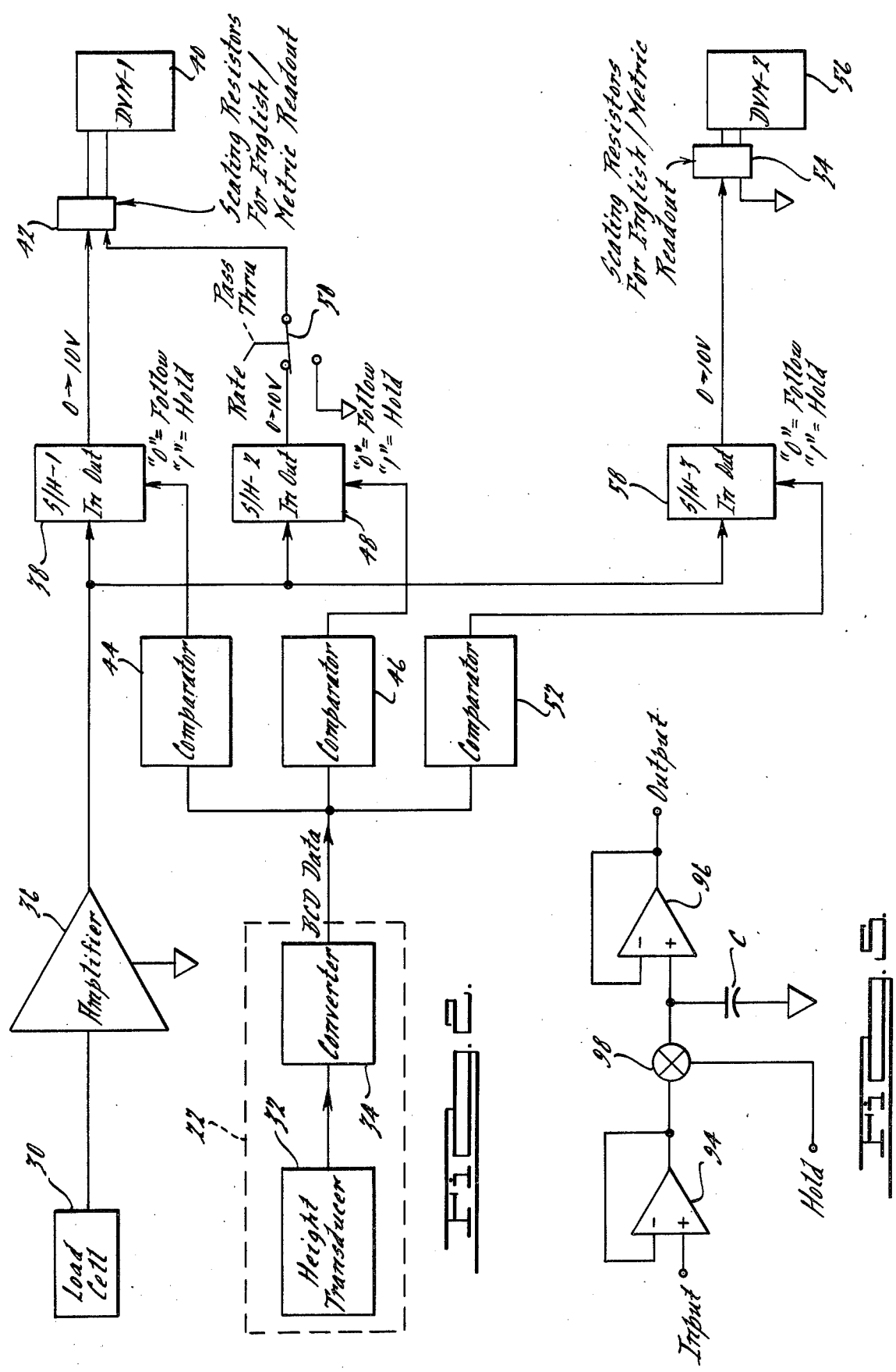
FIG. 2 is a block diagram of the electronic control circuit according to the present invention.

Looking now to FIG. 2, a block diagram of the electronic control circuit according to the present invention is shown. The control circuit has the output from the load cell 30 connected through a high gain amplifier 36 to the inputs of sample and hold circuits 38, 48, and 58. The amplitude of the output signal from the load cell 30 is relatively small; i.e. on the order of 3 millivolts for a five pound load. Thus, in order to raise the signal from the load cell 30 to an appropriate level for displaying on a voltmeter, it is necessary for amplifier 36 to have a gain of approximately 300. With such a high gain factor, it is apparent that amplifier 36 must also have a high degree of stability. Thus, given a force range of between 0 and 50 pounds, the output signal from amplifier 36, in the preferred embodiment herein, will be between 0 and 10 volts.

The height indicator 22 of the preferred embodiment comprises two parts, a height transducer 32 and a converter 34. The height transducer 32 converts the mechanical movement of the ram 12 to a digital pulse train, quadrature output signal, and the converter 34 converts the pulses from the transducer 32 to an equivalent binary coded decimal form (BCD). A height transducer of this type is manufactured by IKL, Incorporated, under the model designation 4082-1. The BCD output from the height indicator 22 is provided to a set of thumbwheel comparators 44, 46 and 52. Each of the comparators 44, 46 and 52 is adapted to be manually preset to the selected height at which a desired force reading is to be taken. When the output signal from height indicator 22 equals any of the preset heights of the comparators 44, 46 and 52, the output line from that comparator will switch from a LO state to a HI state. Thumbwheel comparators of this type are manufactured by ERC Corporation, model designation 2514.

The outputs from comparators 44, 46 and 52, are provided to sample and hold circuits 38, 48 and 58, respectively. The output from sample and hold circuit 38 is provided through a set of scaling resistors 42 to the plus input of a digital voltmeter 40. The output from sample and hold circuit 48 is provided through a toggle switch 50 and scaling resistors 42 to the negative or reference input of digital voltmeter 40. The other terminal of toggle switch 50 is tied to common. As indicated in the figure, the scaling resistors 42 are provided so that the digital voltmeter 40 can display the load reading in units of either pounds or Newtons. The output from each of the sample and hold circuits 38, 48, and 58 is adapted to follow the load signal received at its input from load cell 30. However, when the signal line from its respective comparator 44, 46 or 52 switches to a HI state, the output signal from the sample and hold circuit 38, 48 or 58 is "held" at its current level, notwithstanding further changes in the load signal at its input. In other words, the output from sample and hold circuit 38, for example, will follow the load signal from load cell 30 until the output from height indicator 22 matches the preselected height set on comparator 44.

Accordingly, if it is desired to determine the force reading of a spring when compressed to 1.0 inches, thumbwheel comparator 44 would be set to 1.0 toggle switch 50 would be switched to the "pass through" position, and the height of the spring compressed to less than 1.0 inches. With voltmeter 40 referenced to common by toggle switch 50, the voltmeter 40 will display the output signal from sample and hold circuit 38. Once the spring is compressed past the 1.0 inch check point, the force reading displayed on the voltmeter 40 will correspond to the load of the spring at 1.0 inches.

Similarly, if it is desired to determine the force rate per inch of a spring, thumbwheel comparators 44 and 46 would be set an inch apart, toggle switch 50 would be switched to the "rate" position, and the spring compressed to a height less than the setting on comparator 44. When the height set on comparator 46 is reached, the output of sample and hold circuit 48 will fix the zero reference potential on voltmeter 40. Thus, when the height set on comparator 44 is surpassed, the load reading displayed on voltmeter 40 will equal the difference in the force readings at the respective heights established by the settings on comparators 44 and 46. Since the difference in the height settings on comparators 44 and 46 was initially set at an inch apart, the reading will be equivalent to the spring rate per inch.

Comparator 52, sample and hold circuit 58, and digital voltmeter 56 are optional circuit components. If included in the system, the capability of determining the load at different height settings with a single compression of the spring is provided. Thus, it can be seen that any number of comparators, sample and hold circuits, and digital voltmeters may be added as desired. As an addditional alternative, the output from sample and hold circuit 48 can also be provided through another toggle switch to a separate digital voltmeter so that comparator 46 can also be utilized to set the check point of an additional force reading when a rate measurement is not desired.

Figure 3:
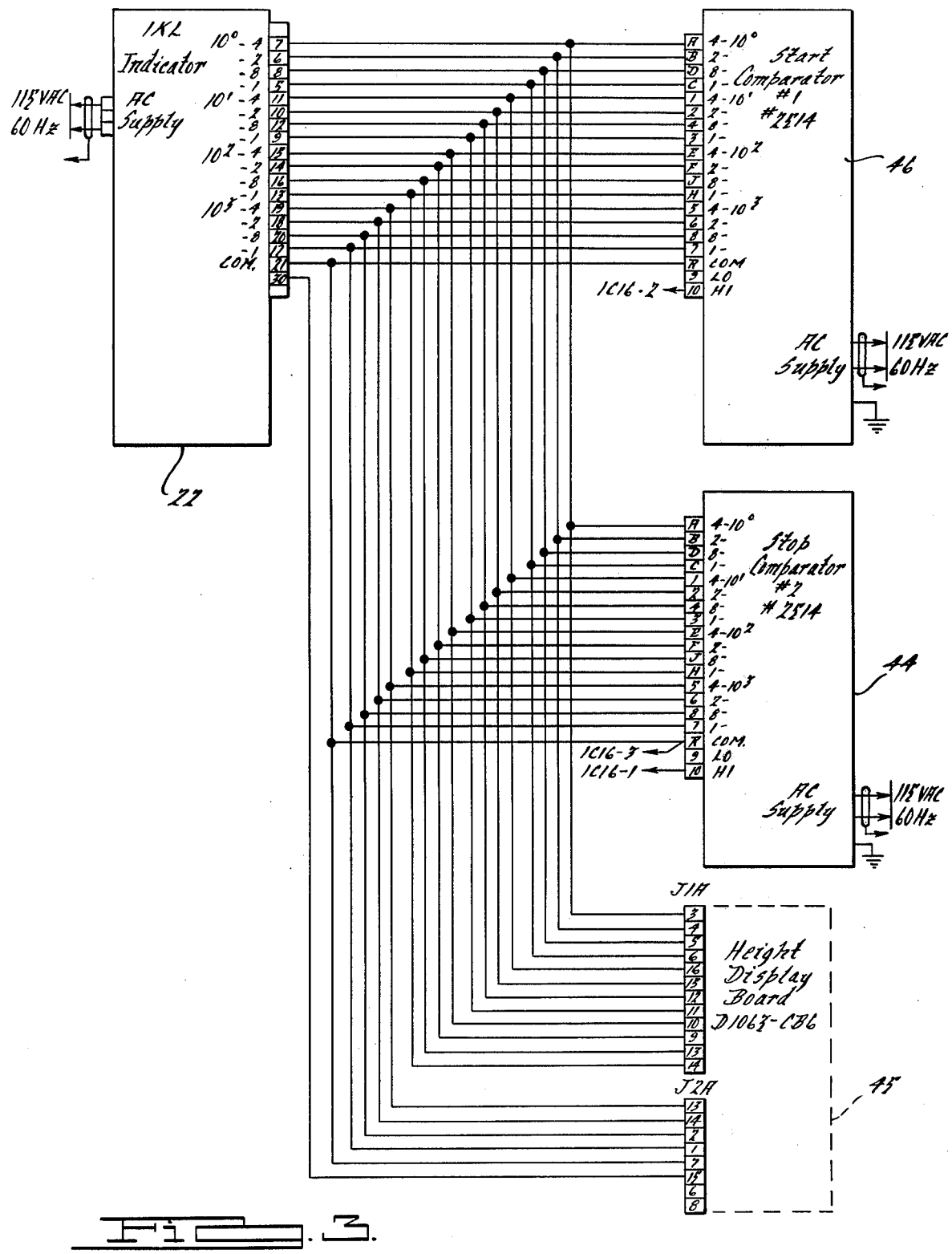
FIG. 3 is a circuit diagram of part of the electronic control circuit of FIG. 2.

Referring now to FIGS. 3 and 4, a detailed circuit diagram of the electronic control circuit according to the present invention is shown. Electrically, the load cell 30 appears as a Wheatstone bridge 60 with its output taken across two of the opposing terminals of the bridge, and the excitation for the bridge being provided across the remaining two terminals. A potentiometer 62 is provided so that the excitation level of the load cell 60 can be adjusted as necessary. The excitation provided to the bridge 60 establishes the magnitude of the signal at the output of the bridge 60 for a given load input. Accordingly, potentiometer 62 is adapted to be initially adjusted to calibrate the system.

The output from the Wheatstone bridge 60 is provided to the input of a high gain operational amplifier 64. The particular amplifier utilized should have a high gain factor, on the order of 300, a high input impedance, and a low voltage drift for changes in temperature. The instrumentation amplifier used in the preferred embodiment is manufactured by Burr-Brown Research Corporation, model designation 3660K-3. A zero adjustment resistor 66 is connected to amplifier 64 so that the output signal from amplifier 64 can be set to zero when the force reading from the load cell 60 corresponds to zero.

The output from amplifier 64 on line 68 is provided to the inputs of three integrated circuits 70, 72 and 82. Each of the integrated circuits 70, 72, and 82 has connected thereto a zero adjustment resistor, 78, 80 and 84, respectively, and a hold capacitor C1, C2, and C3, respectively. The HOLD input terminal (pin 15) of IC 70 is connected through a filter circuit 74 to the HI output terminal (pin 10) of stop comparator 44, shown in FIG. 3. Similarly, the HOLD input terminal (pin 15) of IC 72 is connected through a filter circuit 76 to the HI output terminal (pin 10) of start comparator 46, shown in FIG. 3. The inputs to comparators 44 and 46 are connected to the output of the height indicator 22. As noted in connection with the description of FIG. 2, the height indicator 22 includes a digital pulse-to-BCD converter, so that the output therefrom can be provided directly to the thumbwheel comparators 44 and 46. In addition, if a separate visual display of the output from the height indicator 22 is desired, the output therefrom would also be connected to a height display board 45, as shown. Furthermore, if additional optional comparators are provided, then the output from the height indicator 22 would be routed to these comparators as well. If a third comparator (not shown in FIG. 3) is included, the HI output terminal therefrom would also be connected through a filter circuit 85 to the HOLD input terminal (pin 15) of IC 82. Filter circuits 75, 76, and 85 are provided to prevent transient noise signals from causing ICs 70, 72, and 82 respectively, to inadvertently switch to their HOLD mode.

Each of ICs 70, 72 and 82, together with their associated hold capacitors C1, C2 and C3 respectively, comprise a sample and hold circuit which, as best shown in FIG. 5, consist essentially of a pair of operational amplifiers 94 andd 96, an electronic switch 98, and a hold capacitor C. Sample and hold ICs of this type are manufactured by Harris Corp., model designation HAI-2425. The signal provided to the input of op amp 94 corresponds to the output signal from the high gain amplifier 64 which is directly related to the force reading from the load cell 60. The HOLD signal line connected to the electronic switch 98 corresponds to the HI output terminal from the appropriate height comparator. In operation, the voltage level on capacitor C will follow the input voltage at op amp 94. When the signal on the HOLD line from the comparator goes HI, electronic switch 98 is actuated, thereby opening the circuit between op amp 94 and capacitor C. Accordingly, the output from op amp 96 is held at the voltage level of the capacitor C. The period of time for which capacitor C will maintan this voltage level is dependent upon the size of the capacitor; i.e. the larger the capacitor, the less the drift from the voltage level held. However, if too large a capacitor is selected, the response time of the circuit to changes in the input voltage will be adversely affected. In other words, the larger the capacitor, the greater the time delay before the voltage level on capacitor C will follow the voltage potential at the input of op amp 94. Accordingly, a trade off exists which must be compromised for the particular application involved. A 0.047 mfd capacitor has been found suitable for most purposes.

Returning to FIG. 4, the output from IC 70 on line 71 is provided through a pair of scaling resistors R1 and R2 to the positive input of the digital voltmeter 40. Similarly, the output from IC 72 on line 73 is provided through toggle switch 50 to the negative or reference input of digital voltmeter 40. It will be noted that an additional scaling resistor R3 is connected in series with a relay contact 90 across scaling resistor R1. Relay contact 90 is adapted to be closed when relay coil 88 is energized by the actuation of switch 86. The effect of switching resistor R3 into the circuit is to convert the reading displayed on voltmeter 40 from English to Metric units. Additionally, it will be noted that switch 86 is a double pole switch which when actuated also causes the height indicator 22 to correspondingly provide a metric read-out when the force reading of the voltmeter 40 has been switched to metric units.

The output from the optional third sample and hold IC 82 is provided through a pair of scaling resistors R4 and R5 to the positive input of another digital voltmeter 56. The additional metric scaling resistor R6 is also switched into the circuit when relay contacts 92 are closed upon energization of relay coil 88. Accordingly, it can be seen that the actuation of a single switch 86 causes the entire system to switch from English to Metric units.

While the above description constitutes the preferred embodiments of the invention, it will be appreciated that the invention is susceptible to modification, variation and change without departing from the proper scope or fair meaning of the accompanying claims.

What is claimed is:

1. A device for testing the force of a spring or other compressible object, comprising:
   force transducer means for providing a signal representative of the force exerted by said spring;
   height indicator means for providing a signal representative of the height of said spring;
   compression means for compressing said spring to a height less than a first height;
   first circuit means connected to said force transducer means and said height indicator means for providing and maintaining a first output signal representative of the signal from said force transducer means when the height of said spring corresponded to said first height, including first selector means that are selectably settable to a value which determines said first height; and
   second circuit means connected to said force transducer and said height indicator means for providing and maintaining an output signal representative of the signal from said force transducer means when the height of said spring corresponded to a second height greater than said first height, including second selector means that are selectably settable to a value which determines said second height.

2. The device of claim 1 wherein said compression means are manually operable.

3. The device of claim 1 further including indicator means connected to said first and second circuit means for providing a visual indication of the difference between said first and second output signals.

4. The device of claim 3 wherein said indicator means is further adapted to provide a visual indication of only said first output signal.

5. The device of claim 4 wherein said indicator means includes switch means for selectively determining whether said indicator means will display said first output signal or the differences between said first and second output signals.

6. A device for testing the force of a spring or other compressible object, comprising:

force transducer means for providing a signal representative of the force exerted by said spring;

height indicator means for providing a signal representative of the height of said spring:

comparator means connected to said height indicator means for producing a hold signal when the height of said spring equals a first preselected height including selector means that are selectably settable to a value which determines said first preselected height;

compression means for compressing said spring to a height smaller than said preselected height;

first hold circuit means connected to said force transducer means and said comparator means for providing in response to said hold signal a first output signal representative of the force exerted by said spring at said first preselected height; and indicator means connected to said first hold circuit means for providing a visual representation of said first output signal.

7. The device of claim 6 further including second comparator means responsive to said height indicator means for producing a second hold signal when the height of said spring equals a second preselected height greater than said first preselected height including second selector means that are selectably settable to a value which determines said second preselected height, and second hold circuit means connected to said force transducer means and said second comparator means for providing in response to said second hold signal a second output signal representative of the force exerted by said spring at said second preselected height; said indicator means also being connected to said second hold circuit means for providing a visual representation of the difference between said first and second output signals.

8. The device of claim 7 wherein said indicator means includes switch means for selectively determining whether said indicator means will display said first output signal or the difference between said first and second output signals.

9. The device of claim 8 wherein said indicator means includes a meter having a signal input terminal and a reference input terminal, said signal input terminal being connected to receive said first output signal and said reference input terminal being connected to said switch means so as to receive either said second output signal or a ground signal depending upon the position of said switch means.

10. The device of claim 6 further including second comparator means connected to said height indicator means for producing a second hold signal when the height of said spring equals a second preselected height greater than said first preselected height, second hold circuit means connected to said force transducer means and said second comparator means for providing in response to said second hold signal a second output signal representative of the force exerted by said spring at said second preselected height, and second indicator means connected to said second hold circuit means for providing a visual representation of said second output signal.

11. The device of claim 6 wherein said first hold circuit means comprises a sample and hold circuit that is adapted to provide an output signal that follows the output signal from said force transducer means until said hold signal is received from said comparator means, at which point said hold circuit means maintains the output signal that exists when said hold signal is received notwithstanding further changes in the output signal from said force transducer means.

* * * * *